(12) United States Patent
Chang

(10) Patent No.: US 8,003,558 B2
(45) Date of Patent: Aug. 23, 2011

(54) INTERNAL DONOR FOR OLEFIN POLYMERIZATION CATALYSTS

(75) Inventor: Main Chang, Houston, TX (US)

(73) Assignee: BASF Corporation, Florham Park, NJ (US)

( * ) Notice: Subject to any disclaimer, the term of this patent is extended or adjusted under 35 U.S.C. 154(b) by 85 days.

(21) Appl. No.: 12/181,907

(22) Filed: Jul. 29, 2008

(65) Prior Publication Data

US 2010/0029870 A1    Feb. 4, 2010

(51) Int. Cl.
*B01J 31/00* (2006.01)
*C08F 4/50* (2006.01)

(52) U.S. Cl. ........................................ 502/103; 526/128

(58) Field of Classification Search .................. 526/128; 502/103
See application file for complete search history.

(56) References Cited

U.S. PATENT DOCUMENTS

| | | | |
|---|---|---|---|
| 4,399,054 A | 8/1983 | Ferraris et al. |
| 4,499,194 A | 2/1985 | Harada et al. |
| 4,771,023 A | 9/1988 | Sasaki et al. |
| 4,784,983 A | 11/1988 | Mao et al. |
| 4,816,433 A | 3/1989 | Terano et al. |
| 4,829,038 A | 5/1989 | Hoppin et al. |
| 4,927,797 A | 5/1990 | Ewen |
| 5,153,158 A | 10/1992 | Kioka et al. |
| 5,177,043 A | 1/1993 | Koyama et al. |
| 5,194,531 A | 3/1993 | Toda et al. |
| 5,204,303 A | 4/1993 | Korvenoja et al. |
| 5,221,651 A | 6/1993 | Sacchetti et al. |
| 5,244,989 A | 9/1993 | Hara et al. |
| 5,247,032 A | 9/1993 | Kioka et al. |
| 5,346,972 A | 9/1994 | Duranel et al. |
| 5,374,695 A | 12/1994 | Tanaglia |
| 5,438,110 A | 8/1995 | Ishimaru et al. |
| 5,459,116 A | 10/1995 | Ro et al. |
| 5,489,634 A | 2/1996 | Hara et al. |
| 5,500,396 A | 3/1996 | Martin |
| 5,523,358 A | 6/1996 | Hirose et al. |
| 5,576,259 A | 11/1996 | Hasegawa et al. |
| 5,604,170 A | 2/1997 | Sano et al. |
| 5,684,173 A | 11/1997 | Hosake et al. |
| 5,767,215 A | 6/1998 | Garoff et al. |
| 5,767,216 A | 6/1998 | Frances et al. |
| 5,773,537 A | 6/1998 | Mueller et al. |
| 5,780,562 A | 7/1998 | Shimizu et al. |
| 5,817,590 A | 10/1998 | Hasegawa et al. |
| 5,844,046 A | 12/1998 | Ohgizawa et al. |
| 5,905,050 A | 5/1999 | Koshinen et al. |
| 5,955,396 A | 9/1999 | Lee et al. |
| 5,965,478 A | 10/1999 | Goto et al. |
| 6,054,542 A | 4/2000 | Kojoh et al. |
| 6,075,151 A | 6/2000 | Hauser et al. |
| 6,127,304 A | 10/2000 | Sacchetti et al. |
| 6,291,385 B1 | 9/2001 | Lee et al. |
| 6,323,152 B1 | 11/2001 | Sacchetti et al. |
| 6,407,028 B1 | 6/2002 | Sacchetti et al. |
| 6,417,132 B1 | 7/2002 | Rong et al. |
| 6,437,061 B1 | 8/2002 | Sacchetti et al. |
| 6,469,112 B2 | 10/2002 | Cheng et al. |
| H2060 H | 3/2003 | Spencer et al. |
| 6,627,710 B1 | 9/2003 | Sacchetti et al. |
| 6,630,544 B1 | 10/2003 | Klendworth et al. |
| 6,831,032 B2 | 12/2004 | Spaether |
| 6,962,889 B2 | 11/2005 | Zhu et al. |
| 7,135,531 B2 | 11/2006 | Zhu et al. |
| 7,153,803 B2 | 12/2006 | Zhu et al. |
| 7,326,757 B2 | 2/2008 | Zhu et al. |
| 2002/0035028 A1 | 3/2002 | Jing et al. |

FOREIGN PATENT DOCUMENTS

| | | |
|---|---|---|
| EP | 0018737 | 11/1980 |
| EP | 0642537 | 10/1993 |
| EP | 0860452 | 8/1998 |
| EP | 1273595 | 1/2003 |
| JP | 5494590 | 7/1979 |
| JP | 3-140308 | 6/1991 |
| JP | 2001-114813 | 4/2001 |
| JP | 2001-114814 | 4/2001 |
| JP | 2001-114815 | 4/2001 |
| WO | 93-11164 | 6/1993 |

*Primary Examiner* — David Wu
*Assistant Examiner* — Sonya Wright
(74) *Attorney, Agent, or Firm* — Raymond F. Keller

(57) ABSTRACT

Disclosed are 1,8-naphthyl diaryloates, methods of making 1,8-naphthyl diaryloates, methods of using 1,8-naphthyl diaryloates, solid titanium catalyst components, catalyst systems containing solid titanium catalyst components, methods of making solid titanium catalyst components, and polymerization methods. The solid titanium catalyst components contain a 1,8-naphthyl diaryloate internal electron donor compound. The catalyst system can contain a solid titanium catalyst component, an organoaluminum compound, and an organosilicon compound.

18 Claims, 3 Drawing Sheets

INTERNAL DONOR FOR OLEFIN POLYMERIZATION CATALYSTS

TECHNICAL FIELD

Described are internal electron donors, methods of making internal electron donors, solid titanium catalyst components, catalyst systems containing solid titanium catalyst components, methods of making solid titanium catalyst components, and methods of polymerizing or copolymerizing an alpha-olefin using a catalyst system containing a solid titanium catalyst component.

BACKGROUND

Polyolefins are a class of polymers derived from simple olefins. Known methods of making polyolefins involve the use of Ziegler-Natta polymerization catalysts. These catalysts polymerize vinyl monomers using a transition metal halide to provide a stereoregulated polymer.

Numerous Ziegler-Natta polymerization catalysts exist. The catalysts have different characteristics and/or lead to the production of polyolefins having diverse properties. For example, certain catalysts have high activity while other catalysts have low activity, and similarly certain catalysts have a long life while other catalysts have a short life. Moreover, polyolefins made with the use of Ziegler-Natta polymerization catalysts vary in stereoregularity, molecular weight distribution, impact strength, melt-flowability, rigidity, heat sealability, isotacticity, and the like.

Useful Ziegler-Natta polymerization catalysts made through a precipitation method are made using an organic magnesium compound starting material. The organic magnesium compound leads to the formation of a desirable spherical catalyst particle. Replacing the organic magnesium compound starting material with a markedly less expensive magnesium halide results in a catalyst particle with a morphology that is difficult to control and aspherical or the use of expensive capital processes such as spray congealing (processes where $MgCl_2$ is mixed with ethanol, heated to form a meld, and then sprayed through a nozzle into a cold liquid or gas).

SUMMARY

The following presents a simplified summary of the innovation in order to provide a basic understanding of some aspects of the innovation. This summary is not an extensive overview of the innovation. It is intended to neither identify key or critical elements of the innovation nor delineate the scope of the innovation. Rather, the sole purpose of this summary is to present some concepts of the innovation in a simplified form as a prelude to the more detailed description that is presented hereinafter.

Provided herein are 1,8-naphthyl diaryloate internal electron donor compounds and methods of making and using the 1,8-naphthyl diaryloates. The 1,8-naphthyl diaryloate internal electron donor compounds provide at least one of improved catalyst activity, improved hydrogen response, and improved control over a polymer composition when used in a solid titanium catalyst component of a olefin polymerization catalyst system.

Also provided herein are solid titanium catalyst components for use in olefinic polymerization, olefin polymerization catalyst systems, methods of making solid titanium catalyst components, and methods of polymerizing and copolymerizing olefins involving the use of the solid titanium catalyst components. The solid titanium catalyst components contain a titanium compound, a magnesium compound, and a 1,8-naphthyl diaryloate internal electron donor compound. The catalyst system can contain a solid titanium catalyst component, an organoaluminum compound, and an organosilicon compound. The titanium catalyst component can be made by contacting a magnesium compound and a titanium compound with a 1,8-naphthyl diaryloate internal electron donor compound.

The subject innovation also provides methods of polymerizing or copolymerizing an olefin. The methods involve contacting an olefin with a catalyst system containing a solid titanium catalyst component, an organoaluminum compound; and an organosilicon compound. The solid titanium catalyst component contains a 1,8-naphthyl diaryloate internal electron donor compound.

To the accomplishment of the foregoing and related ends, the innovation involves the features hereinafter fully described and particularly pointed out in the claims. The following description and the annexed drawings set forth in detail certain illustrative aspects and implementations of the innovation. These are indicative, however, of but a few of the various ways in which the principles of the innovation may be employed. Other objects, advantages and novel features of the innovation will become apparent from the following detailed description of the innovation when considered in conjunction with the drawings.

DETAILED DESCRIPTION

Figure 1:
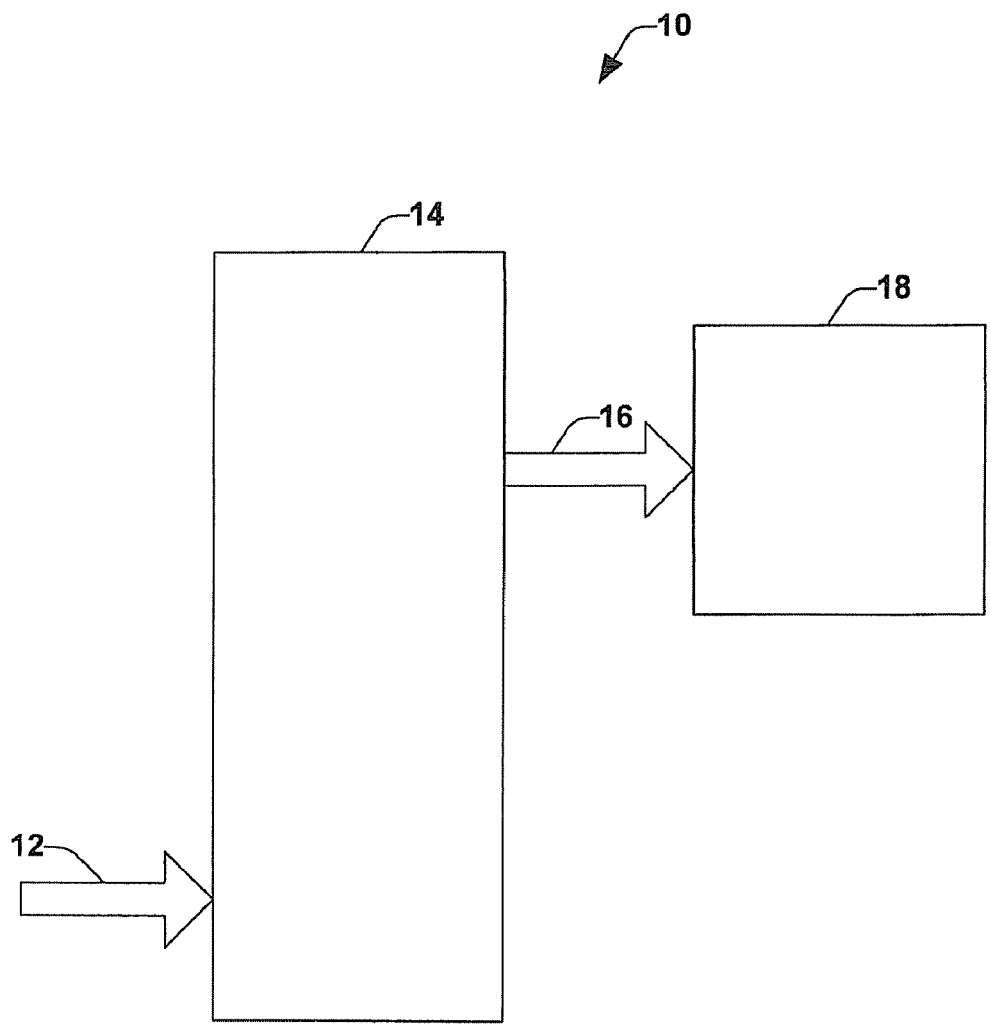
FIG. 1 is a high level schematic diagram of an olefin polymerization system in accordance with one aspect of the subject innovation.

The subject innovation relates to 1,8-naphthyl diaryloate compounds, methods of making 1,8-naphthyl diaryloate compounds, methods of using 1,8-naphthyl diaryloate compounds as internal electron donors, solid titanium catalyst components for use in olefinic polymerization, olefin polymerization catalyst systems, methods of making solid titanium catalyst components, and methods of polymerizing and copolymerizing olefins involving the use of a solid titanium catalyst component.

1,8-naphthyl diaryloate compounds have three aryl groups connected by ester linkages (three aryl groups connected by two ester linkages, such as an aryl-ester linkage-naphthyl-ester linkage-aryl compound).

While not wishing to be bound by any theory, it is believed that the 1,8-naphthyl diaryloate compounds have a chemical structure that permits binding to both a titanium compound and a magnesium compound, both of which are typically present in a solid titanium catalyst component of an olefin polymerization catalyst system. The 1,8-naphthyl diaryloate compounds also act as internal electron donors, owing to the electron donation properties of the compounds, in a solid titanium catalyst component of an olefin polymerization catalyst system.

In one embodiment, the 1,8-naphthyl diaryloate compounds are represented by chemical Formula (I):

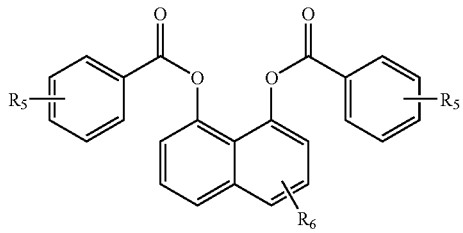

wherein each R is independently hydrogen, halogen, alkyl having 1 to about 8 carbon atoms, phenyl, arylalkyl having 7 to about 18 carbon atoms, or alkylaryl having 7 to about 18 carbon atoms. In another embodiment, each R is independently hydrogen, alkyl having 1 to about 6 carbon atoms, phenyl, arylalkyl having 7 to about 12 carbon atoms, or alkylaryl having 7 to about 12 carbon atoms.

General examples of 1,8-naphthyl diaryloate compounds include 1,8-naphthyl di(alkylbenzoates); 1,8-naphthyl di(dialkylbenzoates); 1,8-naphthyl di(trialkylbenzoates); 1,8-naphthyl di(arylbenzoates); 1,8-naphthyl di(halobenzoates); 1,8-naphthyl di(dihalobenzoates); 1,8-naphthyl di(alkylhalobenzoates); and the like.

Specific examples of 1,8-naphthyl diaryloate compounds include 1,8-naphthyl dibenzoate; 1,8-naphthyl di-4-methylbenzoate; 1,8-naphthyl di-3-methylbenzoate; 1,8-naphthyl di-2-methylbenzoate; 1,8-naphthyl di-4-ethylbenzoate; 1,8-naphthyl di-4-n-propylbenzoate; 1,8-naphthyl di-4-isopropylbenzoate; 1,8-naphthyl di-4-n-butylbenzoate; 1,8-naphthyl di-4-isobutylbenzoate; 1,8-naphthyl di-4-t-butylbenzoate; 1,8-naphthyl di-4-phenylbenzoate; 1,8-naphthyl di-4-fluorobenzoate; 1,8-naphthyl di-3-fluorobenzoate; 1,8-naphthyl di-2-fluorobenzoate; 1,8-naphthyl di-4-chlorobenzoate; 1,8-naphthyl di-3-chlorobenzoate; 1,8-naphthyl di-2-chlorobenzoate; 1,8-naphthyl di-4-bromobenzoate; 1,8-naphthyl di-3-bromobenzoate; 1,8-naphthyl di-2-bromobenzoate; 1,8-naphthyl di-4-cyclohexylbenzoate; 1,8-naphthyl di-2,3-dimethylbenzoate; 1,8-naphthyl di-2,4-dimethylbenzoate; 1,8-naphthyl di-2,5-dimethylbenzoate; 1,8-naphthyl di-2,6-dimethylbenzoate; 1,8-naphthyl di-3,4-dimethylbenzoate; 1,8-naphthyl di-3,5-dimethylbenzoate; 1,8-naphthyl di-2,3-dichlorobenzoate; 1,8-naphthyl di-2,4-dichlorobenzoate; 1,8-naphthyl di-2,5-dichlorobenzoate; 1,8-naphthyl di-2,6-dichlorobenzoate; 1,8-naphthyl di-3,4-dichlorobenzoate; 1,8-naphthyl di-3,5-dichlorobenzoate; 1,8-naphthyl di-3,5-di-t-butylbenzoate; and the like.

1,8-naphthyl diaryloate compounds can be made in any suitable manner such as reacting a naphthyl alcohol with an aryl acid halide having 7 to about 18 carbon atoms. In this connection, one embodiment of a naphthyl alcohol is represented by chemical Formula (II):

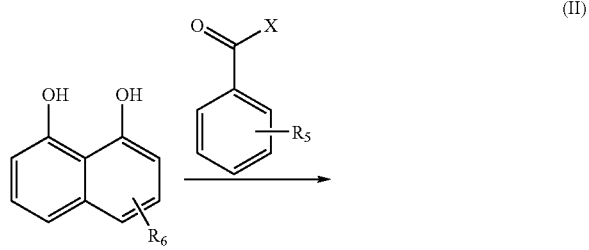

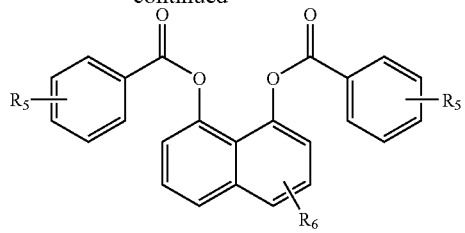

wherein each R is independently hydrogen, halogen, alkyl having 1 to about 8 carbon atoms, phenyl, arylalkyl having 7 to about 18 carbon atoms, or alkylaryl having 7 to about 18 carbon atoms; and X is halogen. In another embodiment, each R is independently hydrogen, alkyl having 1 to about 6 carbon atoms, phenyl, arylalkyl having 7 to about 12 carbon atoms, or alkylaryl having 7 to about 12 carbon atoms; and X is F, Cl, Br, or I.

An aspect of the innovation is solid titanium catalyst components containing a titanium compound, a magnesium compound, and a 1,8-naphthyl diaryloate internal electron donor compound. Use of the 1,8-naphthyl diaryloate internal electron donor compound contributes to improved performance characteristics of resultant catalysts, such as high/improved catalyst activity, high/improved hydrogen response, and the ability to produce polyolefin with desired/controllable xylene solubles values, desired/controllable melt flow indexes (improved polymerization control), and the like.

The solid titanium catalyst component is a highly active catalyst component containing a titanium compound; a magnesium compound; and a 1,8-naphthyl diaryloate internal electron donor compound. The titanium compounds used in the preparation of the solid titanium catalyst component include, for example, a tetravalent titanium compound represented by Formula (III)

$$Ti(OR)_g X_{4-g} \quad (III)$$

wherein each R independently represents a hydrocarbon group, preferably an alkyl group having 1 to about 4 carbon atoms, X represents a halogen atom, and $0 \leq g \leq 4$. Specific examples of the titanium compound include titanium tetrahalides such as $TiCl_4$, $TiBr_4$ and $TiI_4$; alkoxytitanium trihalides such as $Ti(OCH_3)Cl_3$, $Ti(OC_2H_5)Cl_3$, $Ti(O\text{-}n\text{-}C_4H_9)Cl_3$, $Ti(OC_2H_5)Br_3$ and $Ti(O\text{-}i\text{-}C_4H_9)Br_3$; dialkoxytitanium dihalides such as $Ti(OCH_3)_2Cl_2$, $Ti(OC_2H_5)_2Cl_2$, $Ti(O\text{-}n\text{-}C_4H_9)_2Cl_2$ and $Ti(OC_2H_5)_2Br_2$; trialkoxytitanium monohalides such as $Ti(OCH_3)_3Cl$, $Ti(OC_2H_5)_3Cl$, $Ti(O\text{-}n\text{-}C_4H_9)_3Cl$ and $Ti(OC_2H_5)_3Br$; and tetraalkoxytitaniums such as $Ti(OCH_3)_4$, $Ti(OC_2H_5)_4$ and $Ti(O\text{-}n\text{-}C_4H_9)_4$. The titanium compounds may be used individually or in solutions of hydrocarbon compounds or halogenated hydrocarbons.

The magnesium compounds used in the preparation of the solid titanium catalyst component include, for example, a magnesium compound having no reducibility. In one embodiment, the magnesium compound having no reducibility is a halogen containing magnesium compound. Specific examples of the magnesium compound having no reducibility include magnesium halides such as magnesium chloride, magnesium bromide, magnesium iodide and magnesium fluoride; alkoxy magnesium halides such as methoxy magnesium chloride, ethoxy magnesium chloride, isopropoxy magnesium chloride, butoxy magnesium chloride and octoxy magnesium chloride; aryloxy magnesium halides such as phenoxy magnesium chloride and methylphenoxy magnesium chloride; alkoxy magnesiums such as ethoxy magnesium, isopropoxy magnesium, butoxy magnesium, n-octoxy magnesium and 2-ethylhexoxy magnesium; aryloxy magnesiums such as phenoxy magnesium and dimethylphenoxy magnesium; and carboxylic acid salts of magnesium such as magnesium laurate and magnesium stearate. These magnesium compounds may be in the liquid or solid state.

In one aspect, halogen containing magnesium compounds, such as magnesium chloride, alkoxy magnesium chlorides and aryloxy magnesium chlorides, are not employed as the magnesium compound.

When preparing the solid titanium catalyst component, a 1,8-naphthyl diaryloate internal electron donor is used/added. The solid titanium catalyst component can be made by contacting a magnesium compound and a titanium compound with a 1,8-naphthyl diaryloate internal electron donor. In one embodiment, the solid titanium catalyst component is made by contacting a magnesium compound and a titanium compound in the presence of a 1,8-naphthyl diaryloate internal electron donor. In another embodiment, the solid titanium catalyst component is made by forming a magnesium based catalyst support optionally with the titanium compound and optionally with the 1,8-naphthyl diaryloate internal electron donor, and contacting the magnesium based catalyst support with the titanium compound and the 1,8-naphthyl diaryloate internal electron donor. In yet another embodiment, the solid titanium catalyst component is made by contacting a magnesium based catalyst support with the titanium compound to form a mixture, then contacting the mixture with the 1,8-naphthyl diaryloate internal electron donor. In still yet another embodiment, the solid titanium catalyst component is made by contacting a magnesium based catalyst support with the titanium compound to form a mixture, then contacting the mixture with the 1,8-naphthyl diaryloate internal electron donor, then contacting the mixture again with the 1,8-naphthyl diaryloate internal electron donor. Such repeated contact with the 1,8-naphthyl diaryloate internal electron donor can occur once, twice, three times, four times or more, successively or with other acts performed between contact with additional doses of the 1,8-naphthyl diaryloate internal electron donor.

In one embodiment, the solid titanium catalyst compound includes a 1,8-naphthyl diaryloate internal electron donor, but does not include other internal electron donors. In another embodiment, the solid titanium catalyst compound includes other internal electron donor in addition to a 1,8-naphthyl diaryloate internal electron donor. For example, when preparing the solid titanium catalyst component, other internal electron donors such as a dialkyl phthalate, dialkyl succinate, and/or diether can be used/added in addition to a 1,8-naphthyl diaryloate internal electron donor.

Examples of other internal electron donors include oxygen-containing electron donors such as organic acid esters Specific examples include diethyl butylmalonate, diethyl dibutylmalonate, diethyl 1,2-cyclohexanedicarboxylate, di-2-ethylhexyl 1,2-cyclohexanedicarboxylate, methyl benzoate, ethyl benzoate, propyl benzoate, butyl benzoate, octyl benzoate, cyclohexyl benzoate, phenyl benzoate, benzyl benzoate, methyl toluate, ethyl toluate, amyl toluate, ethyl ethylbenzoate, methyl anisate, ethyl anisate, ethyl ethoxybenzoate, diethyl phthalate, dipropyl phthalate, diisopropyl phthalate, dibutyl phthalate, diisobutyl phthalate, dioctyl phthalate, diisononyl phthalate, diethyl succinate, dipropyl succinate, diisopropyl succinate, dibutyl succinate, diisobutyl succinate, dioctyl succinate, diisononyl succinate, and diether compounds such as 1,3-diether compounds.

The internal electron donors may be used individually or in combination. In employing the internal electron donor, they do not have to be used directly as starting materials, but compounds convertible to the electron donors in the course of preparing the titanium catalyst components may also be used as the starting materials.

When making the solid titanium catalyst compound, epoxy compounds can be used. For example, a solid titanium catalyst component is prepared by contacting a magnesium compound with an epoxy compound. The epoxy compounds include compounds having at least one epoxy group in the form of monomers, dimmers, oligomers and polymers. Examples of epoxy compounds include aliphatic epoxy compounds, alicyclic epoxy compounds, aromatic epoxy compounds, or the like. Examples of aliphatic epoxy compounds include halogenated aliphatic epoxy compounds, aliphatic epoxy compounds having a keto group, aliphatic epoxy compounds having an ether bond, aliphatic epoxy compounds having an ester bond, aliphatic epoxy compounds having a tertiary amino group, aliphatic epoxy compounds having a cyano group, or the like. Examples of alicyclic epoxy compounds include halogenated alicyclic epoxy compounds, alicyclic epoxy compounds having a keto group, alicyclic epoxy compounds having an ether bond, alicyclic epoxy compounds having an ester bond, alicyclic epoxy compounds having a tertiary amino group, alicyclic epoxy compounds having a cyano group, or the like. Examples of aromatic epoxy compounds include halogenated aromatic epoxy compounds, aromatic epoxy compounds having a keto group, aromatic epoxy compounds having an ether bond, aromatic epoxy compounds having an ester bond, aromatic epoxy compounds having a tertiary amino group, aromatic epoxy compounds having a cyano group, or the like.

Specific examples of epoxy compounds include epifluorohydrin, epichlorohydrin, epibromohydrin, hexafluoropropylene oxide, 1,2-epoxy-4-fluorobutane, 1-(2,3-epoxypropyl)-4-fluorobenzene, 1-(3,4-epoxybutyl)-2-fluorobenzene, 1-(2,3-epoxypropyl)-4-chlorobenzene, 1-(3,4-epoxybutyl)-3-chlorobenzene, or the like. Specific examples of halogenated alicyclic epoxy compounds include 4-fluoro-1,2-cyclohexene oxide, 6-chloro-2,3-epoxybicyclo[2.2.1]heptane, or the like. Specific examples of halogenated aromatic epoxy compounds include 4-fluorostyrene oxide, 1-(1,2-epoxypropyl)-3-trifluorobenzene, or the like.

In one embodiment, when the solid titanium catalyst component is formed, a surfactant is used. The surfactant can contribute to many of the beneficial properties of the solid titanium catalyst component and catalyst system. General examples of surfactants include polymer surfactants, such as polyacrylates, polymethacrylates, polyalkyl methacrylates, and the like. A polyalkyl methacrylate is a polymer that may contain one or more methacrylate monomers, such as at least two different methacrylate monomers, at least three different methacrylate monomers, etc. Moreover, the acrylate and methacrylate polymers may contain monomers other than acrylate and methacrylate monomers, so long as the polymer surfactant contains at least about 40% by weight acrylate and methacrylate monomers.

In one embodiment, non-ionic surfactants and/or anionic surfactants can be used. Examples of non-ionic surfactants and/or anionic surfactants include phosphate esters, alkyl sulfonates, aryl sulfonates, alkylaryl sulfonates, linear alkyl benzene sulfonates, alkylphenols, ethoxylated alcohols, carboxylic esters, fatty alcohols, fatty esters, fatty aldehydes, fatty ketones, fatty acid nitriles, benzene, naphthalene, anthracene, succinic anhydride, phthalic anhydride, rosin, terpene, phenol, or the like. In fact a number of anhydride surfactants are effective. In some instances, the absence of an anhydride surfactant causes the formation of very small catalyst support particles while the over use creates straw shaped material sometimes referred to as needles.

The solid titanium catalyst component can be formed by contacting the magnesium compound, the titanium compound, and the internal electron donor by known methods used to prepare a highly active titanium catalyst component.

Several examples of the method of producing the solid titanium catalyst component are briefly described below.

(1) The magnesium based catalytic support optionally with the internal electron donor, is reacted with the titanium compound in the liquid phase.

(2) The magnesium based catalytic support and the titanium compounds are reacted in the presence of the internal electron donor to precipitate a solid titanium complex.

(3) The reaction product obtained in (2) is further reacted with the titanium compound.

(4) The reaction product obtained in (1) or (2) is further reacted with the internal electron donor and the titanium compound.

(5) The product obtained in (1) to (4) is treated with a halogen, a halogen compound or an aromatic hydrocarbon.

(6) A magnesium based catalytic support is reacted with the optional internal electron donor, the titanium compound and/or a halogen-containing hydrocarbon.

(7) The magnesium based catalytic support is reacted with the titanium compound in the liquid phase, filtered and washed. The reaction product is further reacted with the internal electron donor and the titanium compound, then activated with additional titanium compound in an organic medium.

In embodiments of making the solid titanium catalyst component according to examples (2), (3), (4) and (5), the magnesium based solution is mixed with a titanium compound such as liquid titanium tetrahalide to form a solid precipitate in the optional presence of an auxiliary precipitant. A polycarboxylic anhydride may be added before, during or after the precipitation of the solids and loaded on the solid.

The process of solids precipitation can be carried out by at least one of three methods. One method involves mixing a titanium compound such as liquid titanium tetrahalide with magnesium based solution at a temperature in the range of about −40 degrees Celsius to about 0 degrees Celsius, and precipitating the solids while the temperature is raised slowly to a range from about 30 degrees Celsius to about 120 degrees Celsius, such as from about 60 degrees Celsius to about 100 degrees Celsius. The second method involves adding a titanium compound dropwise into a magnesium based solution at low or room temperature to precipitate out solids immediately. The third method involves adding a first titanium compound dropwise into a magnesium based solution and mixing a second titanium compound with the magnesium support. In these methods, a 1,8-naphthyl diaryloate internal electron donor can be desirably present in the reaction system. The 1,8-naphthyl diaryloate internal electron donor can be added either after the magnesium based solution is obtained or after the magnesium based catalytic support Is formed. Alternatively auxiliary precipitants can be added to form the magnesium based catalytic support.

The catalyst precursor can be formed in the following way. In a solvent such as toluene, a magnesium and titanium containing solution is seen following the addition of a halogenating agent such as $TiCl_4$ at relatively cooler temperatures, such as −25 degrees Celsius until about 0 degree Celsius. An oil phase is then formed, which can be dispersed into the hydrocarbon phase that is stable until about 40 degrees Celsius. The resultant magnesium material becomes a semi-solid at this point and the particle morphology is now determined. The semi-solid converts to a solid between about 40 degrees Celsius and about 80 degrees Celsius.

To facilitate obtaining uniform solid particles, the process of precipitation can be carried out slowly. When the second method of adding titanium halide dropwise at low or room temperature is applied, the process may take place over a period from about 1 hour to about 6 hours. When the first method of raising the temperature in a slow manner is applied, the rate of temperature increase can range from about 4 degrees Celsius to about 125 degrees Celsius per hour.

The solid precipitate is first separated from the mixture. In the solid precipitate thus obtained may be entrained a variety of complexes and byproducts, so that further treatment may in some instances be necessary. In one embodiment, the solid precipitate is treated with a titanium compound to substantially remove the byproducts from the solid precipitate.

The solid precipitate can be washed with an inert diluent and then treated with a titanium compound or a mixture of a titanium compound and an inert diluent. The titanium compound used in this treatment can be identical to or different with the titanium compound used for forming the solid precipitate. The amount of titanium compound used is from about 1 to about 20 moles, such as from about 2 to about 15 moles, per mole of magnesium compound in the support. The treatment temperature ranges from about 50 degrees Celsius to about 150 degrees Celsius, such as from about 60 degrees Celsius to about 100 degrees Celsius. If a mixture of titanium tetrahalide and inert diluent is used to treat the solid precipitate, the volume % of titanium tetrahalide in the treating solution is from about 10% to about 100%, the rest being an inert diluent.

The treated solids can be further washed with an inert diluent to remove ineffective titanium compounds and other byproducts. The inert diluent herein used can be hexane, heptane, octane, 1,2-dichloroethane, benzene, toluene, ethylbenzene, xylenes, and other hydrocarbons.

By treating the solid precipitate with the titanium compound and optionally an inert diluent, the byproducts in the solid precipitate can be removed from the solid precipitate. In one embodiment, the solid precipitate is treated with the titanium compound and optionally an inert diluent about two times or more and five times or less.

By treating the solid precipitate with an inert diluent, a free titanium compound in the solid precipitate can be removed from the solid precipitate. As a result, the resultant solid precipitate does not substantially contain a free titanium compound. In one embodiment, the solid precipitate is treated repeatedly with an inert diluent until the filtrate contains about 100 ppm or less of titanium. In another embodiment, the solid precipitate is treated repeatedly with an inert diluent until the filtrate contains about 50 ppm or less of titanium. In yet another embodiment, the solid precipitate is treated repeatedly with an inert diluent until the filtrate contains about 10 ppm or less of titanium. In one embodiment, the solid precipitate is treated with an inert diluent about three times or more and seven times or less.

In one embodiment, the solid catalyst component contains from about 0.5 to about 6.0 wt % titanium; from about 10 to about 25 wt % magnesium; from about 40 to about 70 wt % halogen; from about 1 to about 50 wt % 1,8-naphthyl diaryloate internal electron donor; and optionally inert diluent from about 0 to about 15 wt %. In another embodiment, the solid catalyst component contains from about 2 to about 20 wt % of one or more of the 1,8-naphthyl diaryloate internal electron donors. In yet another embodiment, the solid catalyst component contains from about 5 to about 15 wt % of one or more of the 1,8-naphthyl diaryloate internal electron donors.

The amounts of the ingredients used in preparing the solid titanium catalyst component may vary depending upon the method of preparation. In one embodiment, from about 0.01 to about 5 moles of the 1,8-naphthyl diaryloate internal electron donor and from about 0.01 to about 500 moles of the titanium compound are used per mole of the magnesium compound used to make the solid titanium catalyst component. In another embodiment, from about 0.05 to about 2 moles of the 1,8-naphthyl diaryloate internal electron donor and from about 0.05 to about 300 moles of the titanium compound are used per mole of the magnesium compound used to make the solid titanium catalyst component.

In one embodiment, in the solid titanium catalyst component, the atomic ratio of halogen/titanium is from about 4 to about 200; the 1,8-naphthyl diaryloate internal electron donor/titanium mole ratio is from about 0.01 to about 10; and the magnesium/titanium atomic ratio is from about 1 to about 100. In another embodiment, in the solid titanium catalyst component, the atomic ratio of halogen/titanium is from about 5 to about 100; the 1,8-naphthyl diaryloate internal electron donor/titanium mole ratio is from about 0.2 to about 6; and the magnesium/titanium atomic ratio is from about 2 to about 50.

The resulting solid titanium catalyst component generally contains a magnesium halide of a smaller crystal size than commercial magnesium halides and usually has a specific surface area of at least about 50 m$^2$/g, such as from about 60 to 1,000 m$^2$/g, or from about 100 to 800 m$^2$/g. Since, the above ingredients are unified to form an integral structure of the solid titanium catalyst component, the composition of the solid titanium catalyst component does not substantially change by washing with, for example, hexane.

The solid titanium catalyst component may be used after being diluted with an inorganic or organic compound such as a silicon compound, an aluminum compound, or the like.

Methods of preparing solid titanium catalyst components, which can be used in the subject innovation, are described in U.S. Patent Publications and U.S. Pat. Nos. 4,771,023; 4,784,983; 4,829,038; 4,861,847; 4,990,479; 5,177,043; 5,194,531; 5,244,989; 5,438,110; 5,489,634; 5,576,259; 5,767,215; 5,773,537; 5,905,050; 6,323,152; 6,437,061; 6,469,112; 6,962,889; 7,135,531; 7,153,803; 7,271,119; 2004242406; 2004/0242407; and 2007/0021573 which are hereby incorporated by reference in this regard.

The catalyst system may contain at least one organoaluminum compound in addition to the solid titanium catalyst component. Compounds having at least one aluminum-carbon bond in the molecule can be used as the organoaluminum compound. Examples of organoaluminum compounds include compounds of the following Formula (IV)

In Formula (IV), each R independently represents a hydrocarbon group usually having 1 to about 15 carbon atoms, or from 1 to about 4 carbon atoms; X represents a halogen atom, m<3, 0≦p<3, and m+p=3.

Specific examples of the organoaluminum compounds represented by Formula (IV) include trialkyl aluminums such as triethyl aluminum and tributyl aluminum; trialkenyl aluminums such as triisoprenyl aluminum; dialkyl aluminum alkoxides such as diethyl aluminum ethoxide and dibutyl aluminum butoxide; alkyl aluminum sesquialkoxides such as ethyl aluminum sesquiethoxide and butyl aluminum sesquibutoxide; partially alkoxylated alkyl aluminums having an average composition represented by R$^3_{2.5}$Al(OR$^4$)$_{0.5}$; dialkyl aluminum halides such as diethyl aluminum chloride, dibutyl aluminum chloride and diethyl aluminum bromide; alkyl aluminum sesquihalides such as ethyl aluminum sesquichloride, butyl aluminum sesquichloride and ethyl aluminum sesquibromide; partially halogenated alkyl aluminums, for example alkyl aluminum dihalides such as ethyl aluminum dichloride, propyl aluminum dichloride and butyl aluminum dibromide; dialkyl aluminum hydrides such as diethyl aluminum hydride and dibutyl aluminum hydride; other partially hydrogenated alkyl aluminum, for example alkyl aluminum dihyrides such as ethyl aluminum dihydride and propyl aluminum dihydride; and partially alkoxylated and halogenated alkyl aluminums such as ethyl aluminum ethoxychloride, butyl aluminum butoxychloride, and ethyl aluminum ethoxybromide.

The organoaluminum compound catalyst component is used in the catalyst system of the subject innovation in an amount that the mole ratio of aluminum to titanium (from the solid catalyst component) is from about 5 to about 1,000. In another embodiment, the mole ratio of aluminum to titanium in the catalyst system is from about 10 to about 700. In yet another embodiment, the mole ratio of aluminum to titanium in the catalyst system is from about 25 to about 400.

The catalyst system may contain at least one organosilicon compound in addition to the solid titanium catalyst component. This organosilicon compound is sometimes termed an external electron donor. The organosilicon compound contains silicon having at least one hydrocarbon ligand (hydrocarbon group). General examples of hydrocarbon groups include alkyl groups, cycloalkyl groups, (cycloalkyl)methylene groups, alkene groups, aromatic groups, and the like.

The organosilicon compound, when used as an external electron donor serving as one component of a Ziegler-Natta catalyst system for olefin polymerization, contributes to the ability to obtain a polymer (at least a portion of which is polyolefin) having a controllable molecular weight distribution and controllable crystallinity while retaining high performance with respect to catalytic activity.

The organosilicon compound is used in the catalyst system in an amount that the mole ratio of the organoaluminum compound to the organosilicon compound is from about 2 to about 90. In another embodiment, the mole ratio of the organoaluminum compound to the organosilicon compound is from about 5 to about 70. In yet another embodiment, the mole ratio of the organoaluminum compound to the organosilicon compound is from about 7 to about 35.

In one embodiment, the organosilicon compound is represented by Formula (V)

wherein each R and R' independently represent a hydrocarbon group, and n is 0≦n<4.

Specific examples of the organosilicon compound of Formula (V) include trimethylmethoxysilane, trimethylethoxysilane, dimethyldimethoxysilane, dimethyldiethoxysilane, diisopropyldimethoxysilane, diisobutyldimethoxysilane, t-butylmethyldimethoxysilane, t-butylmethyldiethoxysilane, t-amylmethyldiethoxysilane, dicyclopentyldimethoxysilane, diphenyldimethoxysilane, phenylmethyldimethoxysilane, diphenyldiethoxysilane, bis-o-tolyidimethoxysilane, bis-m-tolyldimethoxysilane, bis-p-tolyldimethoxysilane, bis-p-toyidiethoxysilane, bisethylphenyldimethoxysilane, dicyclohexyldimethoxysilane, cyclohexylmethyldimethoxysilane, cyclohexylmethyldiethoxysilane, ethyltrimethoxysilane, ethyltriethoxysilane, vinyltrimethoxysilane, methyltrimethoxysilane, n-propyltriethoxysilane, decyltrimethoxysilane, decyltriethoxysilane, phenyltrimethoxysilane, gamma-chloropropyltrimethoxysilane, methyltriethoxysilane, ethyltriethoxysilane, vinyltriethoxysilane, t-butyltriethoxysilane, n-butyltriethoxysilane, iso-butyltriethoxysilane, phenyltriethoxysilane, gamma-aminopropyltriethoxysilane, chlorotriethoxysilane, ethyltriisopropoxysilane, vinyltributoxysilane, cyclohexyltrimethoxysilane, cyclohexyltriethoxysilane, 2-norbornanetrimethoxysilane, 2-norboranetriethoxysilane, 2-norbornanemethyldimethoxysilane, ethyl silicate, butyl silicate, trimethylphenoxysilane, and methyltriallyloxysilane, In another embodiment, the organosilicon compound is represented by Formula (VI)

$$SiRR'_m(OR'')_{3-m} \qquad (VI)$$

In the above Formula (VI), $0 \leqq m < 3$, such as $0 \leqq m \leqq 2$; and each R independently represents a cyclic hydrocarbon or substituted cyclic hydrocarbon group. Specific examples of the group R include cyclopropyl, cyclobutyl, cyclopentyl, 2-methylcyclopentyl, 3-methylcyclopentyl, 2-ethylcyclopentyl, 3-propylcyclopentyl, 3-isopropylcyclopentyl, 3-butylcyclopentyl, 3-tertiary butyl cyclopentyl, 2,2-dimethylcyclopentyl, 2,3-dimethylcyclopentyl, 2,5-dimethylcyclopentyl, 2,2,5-trimethylcyclopentyl, 2,3,4,5-tetramethylcyclopentyl, 2,2,5,5-tetramethylcyclopentyl, 1-cyclopentylpropyl, 1-methyl-1-cyclopentylethyl, cyclopentenyl, 2-cyclopentenyl, 3-cyclopentenyl, 2-methyl-1-cyclopentenyl, 2-methyl-3-cyclopentenyl, 3-methyl-3-cyclopentenyl, 2-ethyl-3-cyclopentenyl, 2,2-dimethyl-3-cyclopentenyl, 2,5-dimethyl-3-cyclopentenyl, 2,3,4,5-tetramethyl-3-cyclopentenyl, 2,2,5,5-tetramethyl-3-cyclopentenyl, 1,3-cyclopentadienyl, 2,4-cyclopentadienyl, 1,4-cyclopentadienyl, 2-methyl-1,3-cyclopentadienyl, 2-methyl-2,4-cyclopentadienyl, 3-methyl-2,4-cyclopentadienyl, 2-ethyl-2,4-cyclopentadienyl, 2-dimethyl-2,4-cyclopentadienyl, 2,3-dimethyl-2,4-cyclopentadienyl, 2,5-dimethyl-2,4-cyclopentadienyl, 2,3,4,5-tetramethyl-2,4-cyclopentadienyl, indenyl, 2-methylindenyl, 2-ethylindenyl, 2-indenyl, 1-methyl-2-indenyl, 1,3-dimethyl-2-indenyl, indanyl, 2-methylindanyl, 2-indanyl, 1,3-dimethyl-2-indanyl, 4,5,6,7-tetrahydroindenyl, 4,5,6,7-tetrahydro-2-indenyl, 4,5,6,7-tetrahydro-1-methyl-2-indenyl, 4,5,6,7-tetrahydro-1,3-dimethyl-2-indenyl, fluorenyl groups, cyclohexyl, methylcyclohexyls, ethylcyclohexyls, propylcyclohexyls, isopropylcyclohexyls, n-butylcyclohexyls, tertiary-butyl cyclohexyls, dimethylcyclohexyls, and trimethylcyclohexyls.

In Formula (VI), R' and R" are identical or different and each represents a hydrocarbon. Examples of R' and R" are alkyl, cycloalkyl, aryl and aralkyl groups having 3 or more carbon atoms. Furthermore, R and R' may be bridged by an alkyl group, etc. General examples of organosilicon compounds are those of Formula (VI) in which R is a cyclopentyl group, R' is an alkyl group such as methyl or a cyclopentyl group, and R" is an alkyl group, particularly a methyl or ethyl group.

Specific examples of organosilicon compounds of Formula (VI) include trialkoxysilanes such as cyclopropyltrimethoxysilane, cyclobutyltrimethoxysilane, cyclopentyltrimethoxysilane, 2-methylcyclopentyltrimethoxysilane, 2,3-dimethylcyclopentyltrimethoxysilane, 2,5-dimethylcyclopentyltrimethoxysilane, cyclopentyltriethoxysilane, cyclopentenyltrimethoxysilane, 3-cyclopentenyltrimethoxysilane, 2,4-cyclopentadienyltrimethoxysilane, indenyltrimethoxysilane and fluorenyltrimethoxysilane; dialkoxysilanes such as dicyclopentyldimethoxysilane, bis(2-methylcyclopentyl) dimethoxysilane, bis(3-tertiary butylcyclopentyl) dimethoxysilane, bis(2,3-dimethylcyclopentyl) dimethoxysilane, bis(2,5-dimethylcyclopentyl) dimethoxysilane, dicyclopentyldiethoxysilane, dicyclobutyldiethoxysilane, cyclopropylcyclobutyldiethoxysilane, dicyclopentenyldimethoxysilane, di(3-cyclopentenyl)dimethoxysilane, bis(2,5-dimethyl-3-cyclopentenyl)dimethoxysilane, di-2,4-cyclopentadienyidimethoxysilane, bis(2,5-dimethyl-2,4-cyclopentadienyl)dimethoxysilane, bis(1-methyl-1-cyclopentylethyl)dimethoxysilane, cyclopentylcyclopentenyidimethoxysilane, cyclopentylcyclopentadienyldimethoxysilane, diindenyidimethoxysilane, bis(1,3-dimethyl-2-indenyl)dimethoxysilane, cyclopentadienylindenyldimethoxysilane, difluorenyldimethoxysilane, cyclopentylfluorenyldimethoxysilane and indenylfluorenyldimethoxysilane; monoalkoxysilanes such as tricyclopentylmethoxysilane, tricyclopentenylmethoxysilane, tricyclopentadienylmethoxysilane, tricyclopentylethoxysilane, dicyclopentylmethylmethoxysilane, dicyclopentylethylmethoxysilane, dicyclopentylmethylethoxysilane, cyclopentyldimethylmethoxysilane, cyclopentyldiethylmethoxysilane, cyclopentyldimethylethoxysilane, bis(2,5-dimethylcyclopentyl)cyclopentylmethoxysilane, dicyclopentylcyclopentenylmethoxysilane, dicyclopentylcyclopentadienylmethoxysilane and diindenylcyclopentylmethoxysilane; and ethylenebis-cyclopentyldimethoxysilane.

Polymerization of olefins is carried out in the presence of the catalyst system described above. Generally speaking, olefins are contacted with the catalyst system described above under suitable conditions to form desired polymer products. In one embodiment, preliminary polymerization described below is carried out before the main polymerization. In another embodiment, polymerization is carried out without preliminary polymerization. In yet another embodiment, the formation of copolymer is carried out using at least two polymerization zones.

In preliminary polymerization, the solid titanium catalyst component is usually employed in combination with at least a portion of the organoaluminum compound. This may be carried out in the presence of part or the whole of the organosilicon compound (external electron donor). The concentration of the catalyst system used in the preliminary polymerization may be much higher than that in the reaction system of the main polymerization.

In preliminary polymerization, the concentration of the solid titanium catalyst component in the preliminary polymerization is usually from about 0.01 to about 200 millimoles, preferably from about 0.05 to about 100 millimoles, calculated as titanium atoms per liter of an inert hydrocarbon medium described below. In one embodiment, the preliminary polymerization is carried out by adding an olefin and the above catalyst system ingredients to an inert hydrocarbon medium and reacting the olefin under mild conditions.

Specific examples of the inert hydrocarbon medium include aliphatic hydrocarbons such as propane, butane, pentane, hexane, heptane, octane, decane, dodecane and kerosene; alicyclic hydrocarbons such as cyclopentane, cyclohexane and methylcyclopentane; aromatic hydrocarbons such as benzene, toluene and xylene; halogenated hydrocarbons such as ethylene chloride and chlorobenzene; and mixtures thereof. In the subject innovation, a liquid olefin may be used in place of part or the whole of the inert hydrocarbon medium.

The olefin used in the preliminary polymerization may be the same as, or different from, an olefin to be used in the main polymerization.

The reaction temperature for the preliminary polymerization is sufficient for the resulting preliminary polymer to not substantially dissolve in the inert hydrocarbon medium. In one embodiment, the temperature is from about −20 degrees Celsius to about 100 degrees Celsius. In another embodiment, the temperature is from about −10 degrees Celsius to about 80 degrees Celsius. In yet another embodiment, the temperature is from about 0 degrees Celsius to about 40 degrees Celsius.

Optionally, a molecular-weight controlling agent, such as hydrogen, may be used in the preliminary polymerization. The molecular weight controlling agent is used in such an amount that the polymer obtained by the preliminary polymerization has an intrinsic viscosity, measured in decalin at 135 degrees Celsius, of at least about 0.2 dl/g, and preferably from about 0.5 to 10 dl/g.

In one embodiment, the preliminary polymerization is desirably carried out so that from about 0.1 g to about 1,000 g of a polymer forms per gram of the titanium catalyst component of the catalyst system. In another embodiment, the preliminary polymerization is desirably carried out so that from about 0.3 g to about 500 g of a polymer forms per gram of the titanium catalyst component. If the amount of the polymer formed by the preliminary polymerization is too large, the efficiency of producing the olefin polymer in the main polymerization may sometimes decrease, and when the resulting olefin polymer is molded into a film or another article, fish eyes tend to occur in the molded article. The preliminary polymerization may be carried out batchwise or continuously.

After the preliminary polymerization conducted as above, or without performing any preliminary polymerization, the main polymerization of an olefin is carried out in the presence of the above-described olefin polymerization catalyst system formed from the solid titanium catalyst component, the organoaluminum compound and the organosilicon compound (external electron donor).

Examples of olefins that can be used in the main polymerization are alpha-olefins having 2 to 20 carbon atoms such as ethylene (for polyethylene), propylene (for polypropylene), 1-butene (for polybutylene), 4-methyl-1-pentene (for polymethylpentane or PMP), 1-pentene, 1-octene, 1-hexene, 3-methyl-1-pentene, 3-methyl-1-butene, 1-decene, 1-tetradecene, 1-eicosene, and vinylcyclohexane. In the process of the subject innovation, these alpha-olefins may be used individually or in any combination.

In one embodiment, propylene or 1-butene is homopolymerized, or a mixed olefin containing propylene or 1-butene as a main component is copolymerized. When the mixed olefin is used, the proportion of propylene or 1-butene as the main component is usually at least about 50 mole %, preferably at least about 70 mole %.

By performing the preliminary polymerization, the catalyst system in the main polymerization can be adjusted in the degree of activity. This adjustment tends to result in a powdery polymer having a high bulk density. Furthermore, when the preliminary polymerization is carried out, the particle shape of the resulting polymer becomes spherical, and in the case of slurry polymerization, the slurry attains excellent characteristics while in the case of gas phase polymerization, the polymer seed bed attains excellent characteristics. Furthermore, in these embodiments, a polymer having a high stereoregularity index can be produced with a high catalytic efficiency by polymerizing an alpha-olefin having at least about 3 carbon atoms. Accordingly, when producing the propylene copolymer, the resulting copolymer powder or the copolymer becomes easy to handle.

In the homopolymerization or copolymerization of these olefins, a polyunsaturated compound such as a conjugated diene or a non-conjugated diene may be used as a comonomer. Examples of comonomers include styrene, butadiene, acrylonitrile, acrylamide, alpha-methyl styrene, chlorostyrene, vinyl toluene, divinyl benzene, diallylphthalate, alkyl methacrylates and alkyl acrylates. In one embodiment, the comonomers include thermoplastic and elastomeric monomers.

The main polymerization of an olefin is carried out usually in the gaseous or liquid phase. In one embodiment, polymerization (main polymerization) employs a catalyst system containing the titanium catalyst component in an amount from about 0.001 to about 0.75 millimole calculated as Ti atom per liter of the volume of the polymerization zone, the organoaluminum compound in an amount from about 1 to about 2,000 moles per mole of titanium atoms in the titanium catalyst component, and the organosilicon compound (external donor) in an amount from about 0.001 to about 10 moles calculated as Si atoms in the organosilicon compound per mol of the metal atoms in the organoaluminum compound. In another embodiment, polymerization employs a catalyst system containing the titanium catalyst component in an amount from about 0.005 to about 0.5 millimole calculated as Ti atom per liter of the volume of the polymerization zone, the organoaluminum compound in an amount from about 5 to about 500 moles per mole of titanium atoms in the titanium catalyst component, and the organosilicon compound in an amount from about 0.01 to about 2 moles calculated as Si atoms in the organosilicon compound per mol of the metal atoms in the organoaluminum compound. In yet another embodiment, polymerization employs a catalyst system containing the organosilicon compound in an amount from about 0.05 to about 1 mole calculated as Si atoms in the organosilicon compound per mol of the metal atoms in the organoaluminum compound.

When the organoaluminum compound and the organosilicon compound are used partially in the preliminary polymerization, the catalyst system subjected to the preliminary polymerization is used together with the remainder of the catalyst system components. The catalyst system subjected to the preliminary polymerization may contain the preliminary polymerization product.

The use of hydrogen at the time of polymerization promotes and contributes to control of the molecular weight of the resulting polymer, and the polymer obtained may have a high melt flow rate. In this case, the stereoregularity index of the resulting polymer and the activity of the catalyst system are increased according to the methods of the subject innovation.

In one embodiment, the polymerization temperature is from about 20 degrees Celsius to about 200 degrees Celsius. In another embodiment, the polymerization temperature is from about 50 degrees Celsius to about 180 degrees Celsius. In one embodiment, the polymerization pressure is typically from about atmospheric pressure to about 100 $kg/cm^2$. In another embodiment, the polymerization pressure is typically from about 2 $kg/cm^2$ to about 50 $kg/cm^2$. The main polymerization may be carried out batchwise, semi-continuously or continuously. The polymerization may also be carried out in two or more stages under different reaction conditions.

The olefin polymer so obtained may be a homopolymer, a random copolymer, a block copolymer or an impact copolymer. The impact copolymer contains an intimate mixture of a polyolefin homopolymer and a polyolefin rubber. Examples of polyolefin rubbers include ethylene propylene rubbers (EPR) such as ethylene propylene methylene copolymer rubber (EPM) and ethylene propylene diene methylene terpolymer rubber (EPDM).

The olefin polymer obtained by using the catalyst system has a very small amount of an amorphous polymer component and therefore a small amount of a hydrocarbon-soluble component. Accordingly, a film molded from this resultant polymer has low surface tackiness.

The polyolefin obtained by the polymerization process is excellent in particle size distribution, particle diameter and bulk density, and the copolyolefin obtained has a narrow composition distribution. In an impact copolymer, excellent fluidity, low temperature resistance, and a desired balance between stiffness and elasticity can be obtained.

In one embodiment, propylene and an alpha-olefin having 2 or from about 4 to about 20 carbon atoms are copolymerized in the presence of the catalyst system described above. The catalyst system may be one subjected to the preliminary polymerization described above. In another embodiment, propylene and an ethylene rubber are formed in two reactors coupled in series to form an impact copolymer.

The alpha-olefin having 2 carbon atoms is ethylene, and examples of the alpha-olefins having about 4 to about 20 carbon atoms are 1-butene, 1-pentene, 4-methyl-1-pentene, 1-octene, 1-hexene, 3-methyl-1-pentene, 3-methyl-1-butene, 1-decene, vinylcyclohexane, 1-tetradecene, and the like.

In the main polymerization, propylene may be copolymerized with two or more such alpha-olefins. For example, it is possible to copolymerize propylene with ethylene and 1-butene. In one embodiment, propylene is copolymerized with ethylene, 1-butene, or ethylene and 1-butene.

Block copolymerization of propylene and another alpha-olefin may be carried out in two stages. The polymerization in a first stage may be the homopolymerization of propylene or the copolymerization of propylene with the other alpha-olefin. In one embodiment, the amount of the monomers polymerized in the first stage is from about 50 to about 95% by weight. In another embodiment, the amount of the monomers polymerized in the first stage is from about 60 to about 90% by weight. In the subject innovation, this first stage polymerization may, as required be carried out in two or more stages under the same or different polymerization conditions.

In one embodiment, the polymerization in a second stage is desirably carried out such that the mole ratio of propylene to the other alpha-olefin(s) is from about 10/90 to about 90/10. In another embodiment, the polymerization in a second stage is desirably carried out such that the mole ratio of propylene to the other alpha-olefin(s) is from about 20/80 to about 80/20. In yet another embodiment, the polymerization in a second stage is desirably carried out such that the mole ratio of propylene to the other alpha-olefin(s) is from about 30/70 to about 70/30. Producing a crystalline polymer or copolymer of another alpha-olefin may be provided in the second polymerization stage.

The propylene copolymer so obtained may be a random copolymer or the above-described block copolymer. This propylene copolymer typically contains from about 7 to about 50 mole % of units derived from the alpha-olefin having 2 or from about 4 to about 20 carbon atoms. In one embodiment, a propylene random copolymer contains from about 7 to about 20 mole % of units derived from the alpha-olefin having 2 or from about 4 to about 20 carbon atoms. In another embodiment, the propylene block copolymer contains from about 10 to about 50 mole % of units derived from the alpha-olefin having 2 or 4-20 carbon atoms.

In another one embodiment, copolymers made with the catalyst system contain from about 50% to about 99% by weight poly-alpha-olefins and from about 1% to about 50% by weight comonomers (such as thermoplastic or elastomeric monomers). In another embodiment, copolymers made with the catalyst system contain from about 75% to about 98% by weight poly-alpha-olefins and from about 2% to about 25% by weight comonomers.

It should be understood that where there is no reference to the polyunsaturated compound that can be used, the method of polymerization, the amount of the catalyst system and the polymerization conditions, the same description as the above embodiments are applicable.

The catalysts/methods of the subject innovation can in some instances lead to the production of poly-alpha-olefins having xylene solubles (XS) from about 0.5% to about 10%. In another embodiment, poly-alpha-olefins having xylene solubles (XS) from about 1.5% to about 6% are produced in accordance with the subject innovation. XS refers to the percent of solid polymer that dissolves into xylene. A low XS % value generally corresponds to a highly isotactic polymer (i.e., higher crystallinity), whereas a high XS % value generally corresponds to a low isotactic polymer.

In one embodiment, the catalyst efficiency (measured as kilogram of polymer produced per gram of catalyst) of the catalyst system of the subject innovation is at least about 30. In another embodiment, the catalyst efficiency of the catalyst system of the subject innovation is at least about 60.

The catalysts/methods of the subject innovation can in some instances lead to the production of poly-alpha-olefins having melt flow indexes (MFI) from about 0.1 to about 100. The MFI is measured according to ASTM standard D 1238. In another embodiment, poly-alpha-olefins having an MFI from about 5 to about 30 are produced in accordance with the subject innovation. In one embodiment, an impact polypropylene-ethylenepropylene rubber product has an MFI from about 4 to about 10. In another embodiment, an impact polypropylene-ethylenepropylene rubber product has an MFI from about 5 to about 9. In some instances a relatively high MFI indicates that a relatively high catalyst efficiency is obtainable.

The catalysts/methods of the subject innovation can in some instances lead to the production of poly-alpha-olefins having bulk densities (BD) of at least about 0.3 cc/g. In another embodiment, poly-alpha-olefins having a BD of at least about 0.4 cc/g are produced in accordance with the subject innovation.

In one embodiment, an impact polypropylene-ethylenepropylene rubber product having a BD of at least about 0.3 cc/g is produced in accordance with the subject innovation. In another embodiment, an impact polypropylene-ethylenepropylene rubber product having a BD of at least about 0.4 cc/g is produced in accordance with the subject innovation.

The catalysts/methods of the subject innovation lead to the production of poly-alpha-olefins having a relatively narrow molecular weight distribution. In one embodiment, the Mw/Mn of a polypropylene polymer made with the catalyst system is from about 2 to about 6. In another embodiment, the Mw/Mn of a polypropylene polymer made with the catalyst system is from about 3 to about 5.

The subject innovation can lead to the production of a propylene block copolymer and impact copolymers including polypropylene based impact copolymers having one or more of excellent melt-flowability, moldability, desirable balance between rigidity and elasticity, good stereospecific control, good control over polymer particle size, shape, size distribution, and molecular weight distribution, and impact strength with a high catalytic efficiency and/or good operability. Employing the catalyst systems containing the solid titanium catalyst component according to the subject innovation yields catalysts simultaneously having high catalytic efficiency and one or more of excellent melt-flowability, extrudability, moldability, rigidity-elasticity, impact strength and impact strength.

Examples of systems for polymerizing olefins are now described. Referring to FIG. 1, a high level schematic diagram of a system 10 for polymerizing olefins is shown. Inlet 12 is used to introduce into a reactor 14 catalyst system components, olefins, optional comonomers, hydrogen gas, fluid media, pH adjusters, surfactants, and any other additives. Although only one inlet is shown, many often are employed. Reactor 14 is any suitable vehicle that can polymerize olefins. Examples of reactors 14 include a single reactor, a series of two or more reactors, slurry reactors, fixed bed reactors, gas phase reactors, fluidized gas reactors, loop reactors, multizone circulating reactors, and the like. Once polymerization is complete, or as polyolefins are produced, the polymer product is removed from the reactor 14 via outlet 16 which leads to a collector 18. Collector 18 may include downstream processing, such as heating, extrusion, molding, and the like.

Figure 2:
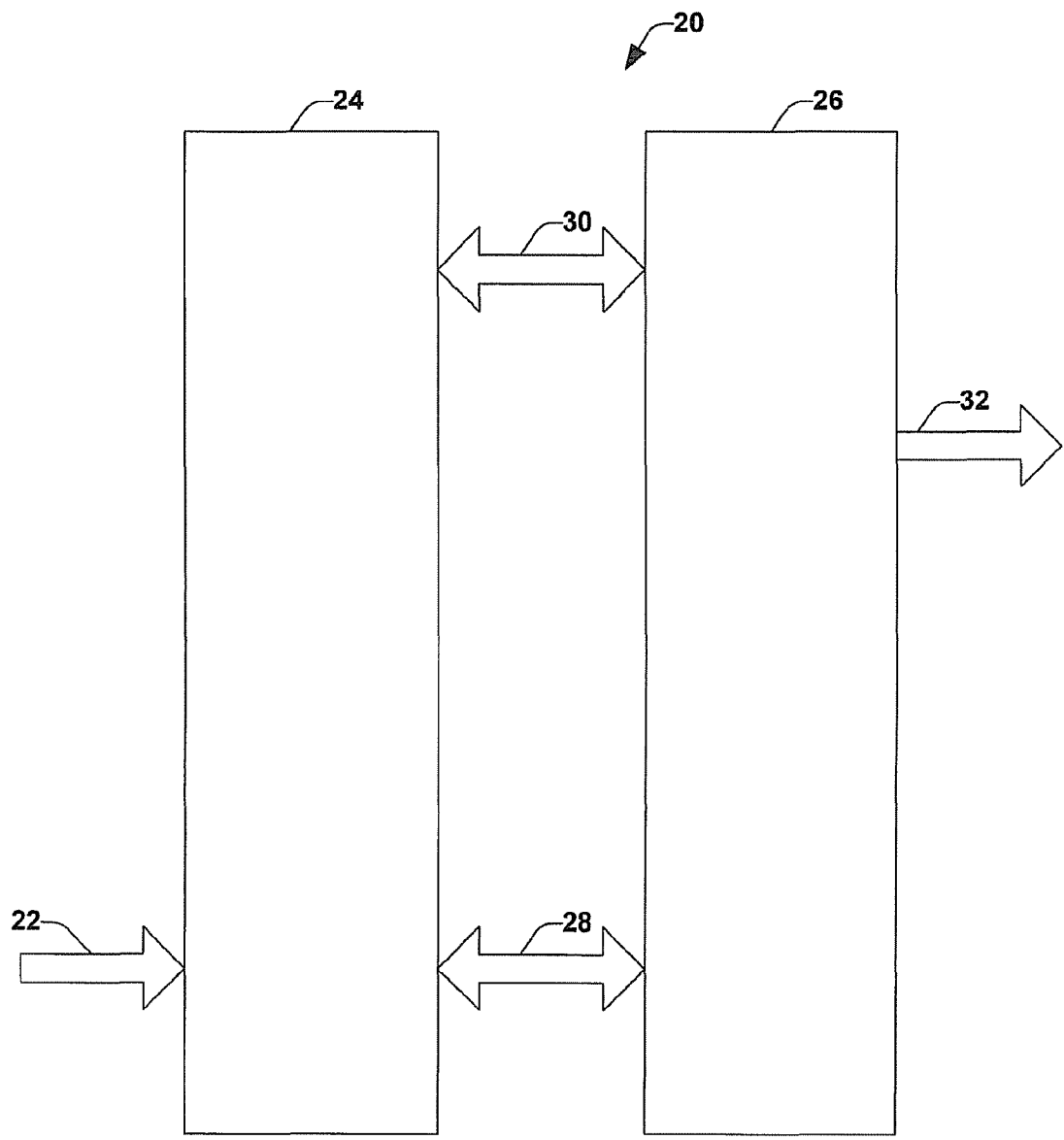
FIG. 2 is a schematic diagram of an olefin polymerization reactor in accordance with one aspect of the subject innovation.
Figure 3:
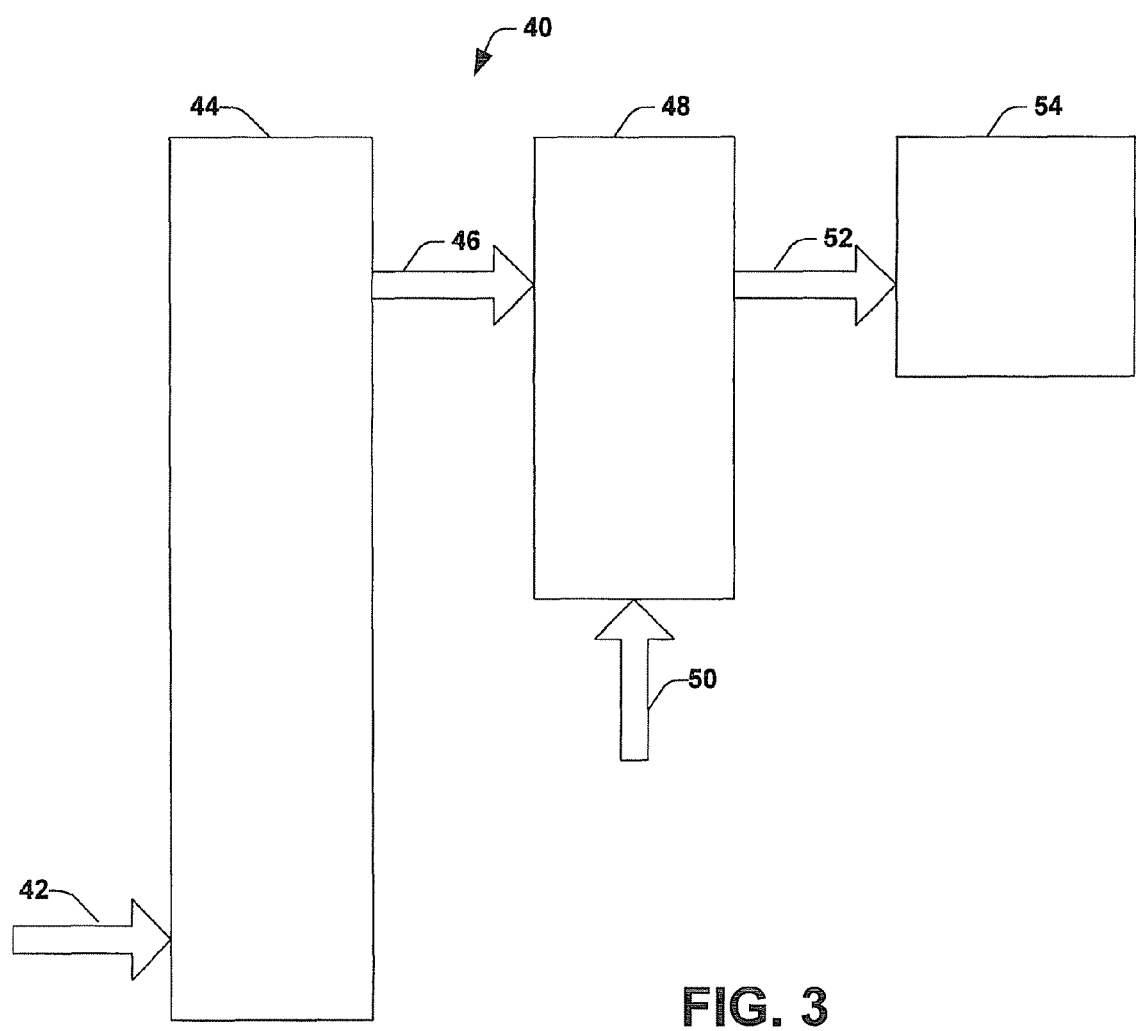
FIG. 3 is a high level schematic diagram of a system for making impact copolymer in accordance with one aspect of the subject innovation.

Referring to FIG. 2, a schematic diagram of a multizone circulating reactor 20 that can be employed as the reactor 14 in FIG. 1 or reactor 44 in FIG. 3 for making polyolefins. The multizone circulating reactor 20 substitutes a series of separate reactors with a single reactor loop that permits different gas phase polymerization conditions in the two sides due to use of a liquid barrier. In the multizone circulating reactor 20, a first zone starts out rich in olefin monomer, and optionally one or more comonomers. A second zone is rich in hydrogen gas, and a high velocity gas flow divides the growing resin particles out loosely. The two zones produce resins of different molecular weight and/or monomer composition. Polymer granules grow as they circulate around the loop, building up alternating layers of each polymer fraction in an onion like fashion. Each polymer particle constitutes an intimate combination of both polymer fractions.

In operation, the polymer particles pass up through the fluidizing gas in an ascending side 24 of the loop and come down through the liquid monomer on a descending side 26. The same or different monomers (and again optionally one or more comonomers) can be added in the two reactor legs. The reactor uses the catalyst systems described above.

In the liquid/gas separation zone 30, hydrogen gas is removed to cool and recirculate. Polymer granules are then packed into the top of the descending side 26, where they then descend. Monomers are introduced as liquids in this section. Conditions in the top of the descending side 26 can be varied with different combinations and/or proportions of monomers in successive passes.

Referring to FIG. 3, a high level schematic diagram of another system 40 for polymerizing olefins is shown. This system is ideally suited to make impact copolymer. A reactor 44, such as a single reactor, a series of reactors, or the multizone circulating reactor is paired with a gas phase or fluidized bed reactor 48 downstream containing the catalyst systems described above to make impact copolymers with desirable impact to stiffness balance or greater softness than are made with conventional catalyst systems. Inlet 42 is used to introduce into the reactor 44 catalyst system components, olefins, optional comonomers, hydrogen gas, fluid media, pH adjusters, surfactants, and any other additives. Although only one inlet is shown, many often are employed. Through transfer means 46 the polyolefin made in the first reactor 44 is sent to a second reactor 48. Feed 50 is used to introduce catalyst system components, olefins, optional comonomers, fluid media, and any other additives. The second reactor 48 may or may not contain catalyst system components. Again, although only one inlet is shown, many often are employed. Once the second polymerization is complete, or as impact copolymers are produced, the polymer product is removed from the second reactor 48 via outlet 52 which leads to a collector 54. Collector 54 may include downstream processing, such as heating, extrusion, molding, and the like. At least one of the first reactor 44 and second reactor 48 contains catalyst systems in accordance with the innovation.

When making an impact copolymer, polypropylene can be formed in the first reactor while an ethylene propylene rubber can be formed in the second reactor. In this polymerization, the ethylene propylene rubber in the second reactor is formed with the matrix (and particularly within the pores) of the polypropylene formed in the first reactor. Consequently, an intimate mixture of an impact copolymer is formed, wherein the polymer product appears as a single polymer product. Such an intimate mixture cannot be made by simply mixing a polypropylene product with an ethylene propylene rubber product.

Although not shown in any of the figures, the systems and reactors can be controlled, optionally with feedback based on continuous or intermittent testing, using a processor equipped with an optional memory and controllers. For example, a processor may be connected to one or more of the reactors, inlets, outlets, testing/measuring systems coupled with the reactors, and the like to monitor and/or control the polymerization process, based on preset data concerning the reactions, and/or based on testing/measuring data generated during a reaction. The controller may control valves, flow rates, the amounts of materials entering the systems, the conditions (temperature, reaction time, pH, etc.) of the reactions, and the like, as instructed by the processor. The processor may contain or be coupled to a memory that contains data concerning various aspects of the polymerization process and/or the systems involved in the polymerization process.

With respect to any figure or numerical range for a given characteristic, a figure or a parameter from one range may be combined with another figure or a parameter from a different range for the same characteristic to generate a numerical range.

Other than in the operating examples, or where otherwise indicated, all numbers, values and/or expressions referring to quantities of ingredients, reaction conditions, etc., used in the specification and claims are to be understood as modified in all instances by the term "about."

The following examples illustrate the subject innovation. Unless otherwise indicated in the following examples and elsewhere in the specification and claims, all parts and percentages are by weight, all temperatures are in degrees Celsius, and pressure is at or near atmospheric pressure.

Example 1

Into a 250 ml Buchi reactor under $N_2$ add a mixture of 3.3 g $MgCl_2$, 0.8 g phthalic anhydride, 50.92 g toluene, 6.41 g epichlorohydrin, and 6.70 g tributylphosphate. The mixture was heated for two hours while agitating at 400 rpm at 60° C. The reaction mixture was then cooled to −30° C. and 37.75 ml of $TiCl_4$ was added slowly while maintaining the reactor temperature below −26° C. After the addition the agitation rate was reduced to 200 rpm and the temperature was ramped from −26° C. to 0° C. in one hour then 0° C. to 85° C. in one hour.

The mixture was held at 85° C. for 30 minute then 1.42 g of 1,8-naphthyl dibenzoate was added (mother liquor addition). The mixture was stirred at 85° C. for one hour then filtered. The solids were re-suspended in 38 ml of toluene and 0.53 g of 1,8-naphthyl dilbenzoate was added to the reactor (toluene addition). The mixture was agitated for one hour at 85° C. and 200 rpm. After filtration and wash twice with 65 ml toluene the mixture was left over night in toluene under $N_2$.

After filtering off the toluene add 66.25 ml of 10-vol % $TiCl_4$ in toluene then heat to and hold at 95° C. with 400 rpm agitation for one hour (1st activation addition). The solids were filtered then re-suspended in 66.25 ml of 10-vol % $TiCl_4$ in toluene. The mixture was hold at 110° C. for thirty minutes after which the solids were once again filtered. This step was repeated two more times. The final catalyst was washed four times with 65 ml of hexane then discharged from the reactor in hexane.

Propylene Polymerization was performed in a 3.4 liter reactor. The reactor was purged at 100° C. under nitrogen for one hour. At room temperature 1.5 ml of 25-wt % TEAI in heptane was added into the reactor. Then 1.0 ml of 0.0768 M solution of cyclohexyl methyl dimethoxy silane followed by 1 ml of 1-wt % catalyst slurry was added into the reactor. The reactor was pressurized with $H_2$ to 3.5 psig then charged with 1500 ml propylene. The reactor was heated to then hold at 70° C. for one hour. At the end of the hold, the reactor was vented and the polymer was recovered.

Yield: 512 g polypropylene. Catalyst activity: 51.2 kg/g; xylene solubles: 1.82%; MFR: 1.7 dg/min.

Example 2

The catalyst was synthesized under same conditions as Example 1 except 0.65 g of 1,8-naphthyl dibenzoate was added in the mother liquor addition stage and 0.24 g of 1,8-naphthyl dibenzoate was added in the toluene addition stage.

Propylene polymerization was the same as in Example 1. Yield: 626 g polypropylene. Catalyst activity: 62.6 kg/g. Xylene solubles: 2.00%. MFR: 0.6 dg/min.

Example 3

The catalyst was synthesized under same conditions as Example 1 except 0.40 g of 1,8-naphthyl dibenzoate was added in the mother liquor addition stage and 0.15 g of 1,8-naphthyl dilbenzoate was added in the toluene addition stage.

Propylene polymerization was the same as in Example 1. Yield: 650 g polypropylene. Catalyst activity: 65 kg/g. Xylene solubles: 4.28%. MFR: 1.6 dg/min.

Example 4

The catalyst was synthesized under same conditions as Example 1 except 0.40 g of 1,8-naphthyl dibenzoate was added in the toluene addition stage and 0.15 g of 1,8-naphthyl dibenzoate was added in the 1st activation stage.

Propylene polymerization was the same as in Example 1. Yield: 475 g polypropylene. Catalyst activity: 47.5 kg/g. Xylene solubles: 2.86%. MFR: 0.8 dg/min.

Example 5

The catalyst was synthesized under same conditions as Example 1 except 0.30 g of 1,8-naphthyl dibenzoate was added in the toluene addition stage and 0.25 g of 1,8-naphthyl dibenzoate was added in the 1st activation stage.

Propylene polymerization was the same as in Example 1. Yield: 505 g polypropylene. Catalyst activity: 50.5 kg/g. Xylene solubles: 3.26%. MFR: 0.9 dg/min.

Example 6

The catalyst was synthesized under same conditions as Example 1 except 1.4 g of 1,8-naphthyl dibenzoate was added in the mother liquor addition stage, 0.53 g of 1,8-naphthyl dibenzoate was added in the toluene addition stage and 0.3 g of 1,8-naphthyl dilbenzoate was added in the 1st activation stage.

Propylene polymerization was the same as in Example 1. Yield: 454 g polypropylene. Catalyst activity: 45.4 kg/g. Xylene solubles: 1.97%. MFR: 0.07 dg/min.

Example 7

The catalyst was synthesized under same conditions as Example 1 except 0.70 g of 1,8-naphthyl di-4-methylbenzoate was added in the mother liquor addition stage and 0.26 g of 1,8-naphthyl di-4-methylbenzoate was added in the toluene addition stage.

Propylene polymerization was the same as in Example 1. Yield: 595 g polypropylene. Catalyst activity: 59.5 kg/g. Xylene solubles: 2.65%. MFR: 2.2 dg/min.

Example 8

The catalyst was synthesized under same conditions as Example 1 except 0.43 g of 1,8-naphthyl di-4-methylbenzoate was added in the toluene addition stage and 0.16 g of 1,8-naphthyl di-4-methylbenzoate was added in the 1st activation stage.

Propylene polymerization was the same as in Example 1. Yield: 476 g polypropylene. Catalyst activity: 47.6 kg/g. Xylene solubles: 2.69%. MFR: 0.8 dg/min.

Example 9

The catalyst was synthesized under same conditions as Example 1 except 0.323 g of 1,8-naphthyl di-4-methylbenzoate was added in the toluene addition stage and 0.27 g of 1,8-naphthyl di-4-methylbenzoate was added in the 1st activation stage.

Propylene polymerization was the same as in Example 1. Yield: 494 g polypropylene. Catalyst activity: 49.4 kg/g. Xylene solubles: 2.74%. MFR: 1.1 dg/min.

Example 10

A catalyst was synthesized under same conditions as Example 1 except 0.59 g of 1,8-naphthyl di-2-methylbenzoate was added only in the mother liquor addition stage and only the first three $TiCl_4$ activations were carried out.

Propylene polymerization was the same as in Example 1. Yield: 618 g polypropylene. Catalyst activity: 61.8 kg/g. Xylene solubles: 3.88%. MFR: 0.9 dg/min.

Example 11

A catalyst was synthesized under same conditions as Example 1 except 0.59 g of 1,8-naphthyl di-3-methylbenzoate was added only in the mother liquor addition stage and only the first three $TiCl_4$ activations were carried out.

Propylene polymerization was the same as in Example 1. Yield: 545 g polypropylene. Catalyst activity: 54.5 kg/g. Xylene solubles: 3.38%. MFR: 1.3 dg/min.

Example 12

A catalyst was synthesized under same conditions as Example 1 except 0.44 g and 0.16 g of 1,8-naphthyl di-4- fluorolbenzoate were added in the mother liquor and toluene addition stage, respectively. Also only the first two TiCl$_4$ activations were carried out.

Propylene polymerization was the same as in Example 1. Yield: 573 g polypropylene. Catalyst activity: 57.3 kg/g. Xylene solubles: 2.99%. MFR: 0.9 dg/min.

What has been described above includes examples of the disclosed information. It is, of course, not possible to describe every conceivable combination of components or methodologies for purposes of describing the disclosed information, but one of ordinary skill in the art can recognize that many further combinations and permutations of the disclosed information are possible. Accordingly, the disclosed information is intended to embrace all such alterations, modifications and variations that fall within the spirit and scope of the appended claims. Furthermore, to the extent that the term "includes," "has," "involve," or variants thereof is used in either the detailed description or the claims, such term is intended to be inclusive in a manner similar to the term "comprising" as "comprising" is interpreted when employed as a transitional word in a claim.

What is claimed is:

1. A solid titanium catalyst component for use in olefinic polymerization, comprising:
    a titanium compound;
    a magnesium compound; and
    a 1,8-naphthyl diaryloate internal electron donor compound.

2. The solid titanium catalyst component of claim 1, wherein the 1,8-naphthyl diaryloate internal electron donor compound is represented by chemical Formula (I):

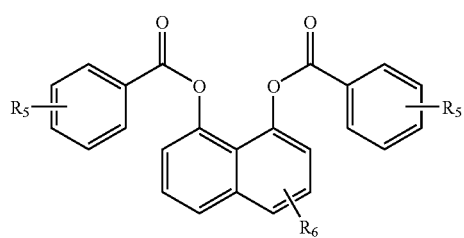

wherein each R is independently hydrogen, halogen, alkyl having 1 to 8 carbon atoms, phenyl, arylalkyl having 7 to 18 carbon atoms, or alkylaryl having 7 to about 18 carbon atoms.

3. The solid titanium catalyst component of claim 1 comprising from about 1 to about 50 wt % of the 1,8-naphthyl diaryloate internal electron donor compound.

4. The solid titanium catalyst component of claim 1, wherein the 1,8-naphthyl diaryloate internal electron donor compound comprises at least one selected from the group consisting of 1,8-naphthyl dibenzoate; 1,8-naphthyl di-4-methylbenzoate; 1,8-naphthyl di-3-methylbenzoate; 1,8-naphthyl di-2-methylbenzoate; 1,8-naphthyl di-4-ethylbenzoate; 1,8-naphthyl di-4-n-propylbenzoate; 1,8-naphthyl di-4-isopropylbenzoate; 1,8-naphthyl di-4-n-butylbenzoate; 1,8-naphthyl di-4-isobutylbenzoate; 1,8-naphthyl di-4-t-butylbenzoate; 1,8-naphthyl di-4-phenylbenzoate; 1,8-naphthyl di-4-fluorobenzoate; 1,8-naphthyl di-3-fluorobenzoate; 1,8-naphthyl di-2-fluorobenzoate; 1,8-naphthyl di-4-chlorobenzoate, 1,8-naphthyl di-3-chlorobenzoate; 1,8-naphthyl di-2-chlorobenzoate; 1,8-naphthyl di-4-bromobenzoate; 1,8-naphthyl di-3-bromobenzoate; 1,8-naphthyl di-2-bromobenzoate; 1,8-naphthyl di-4-cyclohexylbenzoate; 1,8-naphthyl di-2,3-dimethylbenzoate; 1,8-naphthyl di-2,4-dimethylbenzoate; 1,8-naphthyl di-2,5-dimethylbenzoate; 1,8-naphthyl di-2,6-dimethylbenzoate; 1,8-naphthyl di-3,4-dimethylbenzoate; 1,8-naphthyl di-3,5-dimethylbenzoate; 1,8-naphthyl di-2,3-dichlorobenzoate; 1,8-naphthyl di-2,4-dichlorobenzoate; 1,8-naphthyl di-2,5-dichlorobenzoate; 1,8-naphthyl di-2,6-dichlorobenzoate; 1,8-naphthyl di-3,4-dichlorobenzoate; 1,8-naphthyl di-3,5-dichlorobenzoate; and 1,8-naphthyl di-3,5-di-t-butylbenzoate.

5. A method of making the solid titanium catalyst component of claim 1 for a catalyst system, comprising:
    contacting a magnesium compound and a titanium compound with a 1,8-naphthyl diaryloate internal electron donor compound to provide the solid titanium catalyst component.

6. The method of claim 5, wherein the 1,8-naphthyl diaryloate internal electron donor compound is represented by chemical Formula (I):

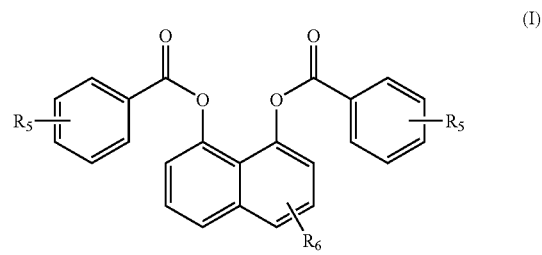

wherein each R is independently hydrogen, halogen, alkyl having 1 to 8 carbon atoms, phenyl, arylalkyl having 7 to 18 carbon atoms, or alkylaryl having 7 to about 18 carbon atoms.

7. The method of claim 5 further comprising contacting the magnesium compound and the titanium compound with a second 1,8-naphthyl diaryloate internal electron donor compound to provide the solid titanium catalyst component.

8. The method of claim 5, wherein each R is independently hydrogen, halogen, alkyl having 1 to 6 carbon atoms, or phenyl.

9. The solid titanium catalyst component of claim 2, wherein each R is independently hydrogen, halogen, alkyl having 1 to 6 carbon atoms, phenyl, arylalkyl having 7 to 12 carbon atoms, or alkylaryl having 7 to 12 carbon atoms.

10. The solid titanium catalyst component of claim 1, wherein the 1,8-naphthyl diaryloate internal electron donor compound comprises at least one selected from the group consisting of 1,8-naphthyl dibenzoate and 1,8-naphthyl di-4-methylbenzoate.

11. The solid titanium catalyst component of claim 2, wherein each R is independently hydrogen, halogen, alkyl having 1 to 6 carbon atoms, or phenyl.

12. The solid titanium catalyst component of claim 1 comprising from about 2 to about 20 wt % of the 1,8-naphthyl diaryloate internal electron donor compound.

13. A solid titanium catalyst component for use in olefinic polymerization, comprising:
    a titanium compound;
    a magnesium compound; and
    1,8-naphthyl dibenzoate as an internal electron donor compound.

14. The solid titanium catalyst component of claim 13 comprising from about 1 to about 50 wt % of the 1,8-naphthyl dibenzoate internal electron donor compound.

15. The solid titanium catalyst component of claim 13 comprising from about 2 to about 20 wt % of the 1,8-naphthyl dibenzoate internal electron donor compound.

16. The method of claim 6, wherein each R is independently hydrogen, halogen, alkyl having 1 to 6 carbon atoms, phenyl, arylalkyl having 7 to 12 carbon atoms, or alkylaryl having 7 to 12 carbon atoms.

17. The method of claim 5, wherein the 1,8-naphthyl diaryloate internal electron donor compound comprises at least one selected from the group consisting of 1,8-naphthyl dibenzoate; 1,8-naphthyl di-4-methylbenzoate; 1,8-naphthyl di-3-methylbenzoate; 1,8-naphthyl di-2-methylbenzoate; 1,8-naphthyl di-4-ethylbenzoate; 1,8-naphthyl di-4-n-propylbenzoate; 1,8-naphthyl di-4-isopropylbenzoate; 1,8-naphthyl di-4-n-butylbenzoate; 1,8-naphthyl di-4-isobutylbenzoate; 1,8-naphthyl di-4-t-butylbenzoate; 1,8-naphthyl di-4-phenylbenzoate; 1,8-naphthyl di-4-fluorobenzoate; 1,8-naphthyl di-3-fluorobenzoate; 1,8-naphthyl di-2-fluorobenzoate; 1,8-naphthyl di-4-chlorobenzoate; 1,8-naphthyl di-3-chlorobenzoate; 1,8-naphthyl di-2-chlorobenzoate; 1,8-naphthyl di-4-bromobenzoate; 1,8-naphthyl di-3-bromobenzoate; 1,8-naphthyl di-2-bromobenzoate; 1,8-naphthyl di-4-cyclohexylbenzoate; 1,8-naphthyl di-2,3-dimethylbenzoate; 1,8-naphthyl di-2,4-dimethylbenzoate; 1,8-naphthyl di-2,5-dimethylbenzoate; 1,8-naphthyl di-2,6-dimethylbenzoate; 1,8-naphthyl di-3,4-dimethylbenzoate; 1,8-naphthyl di-3,5-dimethylbenzoate, 1,8-naphthyl di-2,3-dichlorobenzoate; 1,8-naphthyl di-2,4-dichlorobenzoate; 1,8-naphthyl di-2,5-dichlorobenzoate; 1,8-naphthyl di-2,6-dichlorobenzoate, 1,8-naphthyl di-3,4-dichlorobenzoate; 1,8-naphthyl di-3,5-dichlorobenzoate; and 1,8-naphthyl di-3,5-di-t-butylbenzoate.

18. The method of claim 5, wherein the 1,8-naphthyl diaryloate internal electron donor compound comprises at least one selected from the group consisting of 1,8-naphthyl dibenzoate and 1,8-naphthyl di-4-methylbenzoate.

\* \* \* \* \*